(12) United States Patent
Biryukov et al.

(10) Patent No.: US 6,783,957 B1
(45) Date of Patent: Aug. 31, 2004

(54) METHOD FOR SYNTHESIS OF POLYPEPTIDES IN CELL-FREE SYSTEMS

(75) Inventors: Sergey Vladimirovich Biryukov, Moscow Region (RU); Peter Nikolaevich Simonenko, deceased, late of Moscow Region (RU), Aleno Simonenka, legal representative; Vladimir Anatolievich Shirokov, Moscow Region (RU); Alexander Sergeyevich Spirin, Moscow Region (RU)

(73) Assignees: Roche Diagnostics GmbH (DE); Institute of Protein Research (RU)

( * ) Notice: Subject to any disclaimer, the term of this patent is extended or adjusted under 35 U.S.C. 154(b) by 0 days.

(21) Appl. No.: 09/937,474

(22) PCT Filed: Mar. 22, 2000

(86) PCT No.: PCT/EP00/02508

§ 371 (c)(1),
(2), (4) Date: Jan. 21, 2003

(87) PCT Pub. No.: WO00/58493

PCT Pub. Date: Oct. 5, 2000

(30) Foreign Application Priority Data

Mar. 25, 1999 (RU) .......................................... 99106754

(51) Int. Cl.[7] .............................................. C12P 21/00
(52) U.S. Cl. .................................. 435/69.1; 536/26.26
(58) Field of Search ........................... 935/17, 36, 39, 935/44; 435/7.2, 69.1; 536/26.26

(56) References Cited

U.S. PATENT DOCUMENTS

| | | | |
|---|---|---|---|
| 4,668,624 A | 5/1987 | Roberts ....................... | 435/68 |
| 4,937,190 A | 6/1990 | Palmenberg et al. ........ | 435/69.1 |
| 5,135,853 A | 8/1992 | Dziewulski et al. .......... | 435/41 |
| 5,324,428 A | 6/1994 | Flaherty ...................... | 210/232 |
| 5,324,637 A | 6/1994 | Thompson et al. ......... | 435/68.1 |
| 5,434,079 A | 7/1995 | Mozayeni .................... | 435/311 |
| 5,478,730 A | 12/1995 | Alakhov et al. | |
| 5,503,741 A | 4/1996 | Clark .......................... | 210/232 |
| 5,593,856 A | 1/1997 | Choi et al. | |
| 5,674,729 A | 10/1997 | Wimmer et al. .......... | 435/235.1 |
| 5,807,717 A | 9/1998 | Joyce .......................... | 435/91.1 |
| 6,107,055 A | 8/2000 | Bauer et al. ................ | 435/68.1 |

FOREIGN PATENT DOCUMENTS

| | | |
|---|---|---|
| EP | 0312617 B1 | 4/1989 |
| EP | 0398083 A1 | 11/1990 |
| EP | 0401369 B1 | 12/1990 |
| EP | 0485608 B1 | 5/1992 |
| EP | 0593757 B1 | 4/1994 |
| EP | 0894852A2 A3 | 2/1999 |
| JP | 05-076381 | 3/1993 |
| JP | 07-031494 | 7/1993 |
| JP | 07-075592 | 3/1995 |
| JP | 10-080295 | 3/1998 |
| WO | WO 93/07287 | 4/1993 |
| WO | WO 94/18371 | 8/1994 |
| WO | WO 98/02532 | 1/1998 |
| WO | WO 99/50436 | 10/1999 |

OTHER PUBLICATIONS

Alberts B. et al., "Intracellular Membranes Increases the Rates of Diffusion–limited Reactions", New York/London 1983, Protein Function, p. 133.

Baranov et al, "Gene Expression in Cell–Free System on Preparative Scale", Methods in Enzymology. vol. 217. pp. 123–142.

Dong–Myung Kim, et al., "A Semicontinuous Prokaryotic Coupled Transcription/Translation System Using a Dialysis Membrane", Biotechnol. Prog. 1996, 12, 645–649, XP–002106860.

Baranov et al., "Gene expression in a cell–free system on the preparative scale", Gene, 84(1989) 463–466.

Craig, et al., "Plasmid cDNA–directed protein synthesis in a coupled eukaryotic in vitro transcription–translation system", Nucleic Acids Research, vol. 20, No. 19 4987–4995.

Davis. et al., "Large Scale Dialysis Reactions Using E. Coili S30 Extract Sytems", Promega Notes (p. 14–21).

Kleinkauf et al., "First German–Russian Summerschool on In Vitro Systems", Technical University Berlin Institute of Biochemistry and Molecular Biology Sep. 28–30, 1994 (p. 63–70).

Guajardo et al., "NTP Concentration Effects on Initial Transcription by T7 RNAP Indicate that Translocation Occurs through Passive Sliding and Reveal that Divergent Promoters have Distinct NTP Concentration Requirements for Productive Initiation", J. Mol. Biol. (1998) 281, 777–792.

Gurevich, et al., "Preparative in Vitro mRNA Synthesis Using SP6 and T7 RNA Polymerases", Analytical Biochemistry 195, 207–213 (1991).

Kern et al., "Application of Solution Equilibrium Analysis to in Vitro RNA Transcription", Biotechnol. Prog. 1997, 13, 747–756.

(List continued on next page.)

*Primary Examiner*—Robert A. Wax
(74) *Attorney, Agent, or Firm*—Marilyn Amick; Roche Diagnostics Corporation

(57) ABSTRACT

The method of polypeptide synthesis in eukaryotic or porkaryotic cell-free systems based on a modified verion of synthesis in the continuous flow or continuous exchange modes when, in addition to input into the reaction mixture of components maintaining the synthesis and removal from the reaction mixture of low molecular weight components inhibiting the synthesis, the concentration of at least one of the components selected from the group consisting of $Mg^{2+}$, $K^+$, NTP, polyamines or their combinations determining the productivity of the synthesis is continuously changed within the given range of concentrations, while the concentrations of the other components are maintained constant.

9 Claims, 7 Drawing Sheets

OTHER PUBLICATIONS

Kigawa et al., "A Continuous Cell–Free protein Synthesis System for Coupled Transcription–Translation", J. Biochem. 110, 166–168 (1991).

Laios et al., "Novel Hybridization Assay Configuration Based on In Vitro Expression of DNA Reporter Molecules", Clinical Biochemistry, vol. 31, No. 3, 151–158, Apr. 1988.

Maier et al., "Strep–Tag II Affinity Purification: An Approach to Study Intermediates of Metalloenzyme Biosynthesis", Analytical, Biochemistry 259, 68–73 (1998).

Martemyanov et al., "Direct expression of PCR products in a cell–free transcription/translation system: synthesis of antibacterial peptide cecropin", FEBS Letters 414 (1997) 268–270.

Merrick, "Translation of Exogenous mRNAs in reticulocyte Lysates", Methods in Enzymology, vol. 101, Monitoring Cloned Gene Expression pp. 606–615.

Pelham et al., "An Efficient mRNA–Dependent Translation System from Reticulocyte Lysates", Eur. J. Biochem. 67, 247–256 (1976).

Pokrovskaya et al., "In Vitro Transcription: Preparative RNA Yields in Analytical Scale Reactions", Analytical Biochemistry 220, 420–423 (1994).

Roberts et al., "Efficient Translation of Tobacco Mosaic Virus RNA and Rabbit Globin 9S RNA in a Cell–Free System from Commercial Wheat Germ", Proc. Nat. Acad. Sci. USA vol. 70, No. 8, pp. 2330–2334, Aug. 1973.

Ryabova et al., "Preparative synthesis of globin in a continuous cell–free translation system from rabbit reticulocytes", vol. 17, No. 11, 1989, p. 4412.

Ryabova et al., "Continuous–Flow Cell–Free Translation, Transcription–Translation, and Replication–Translation Systems", vol. 77 (8) pgs.

Spirin et al., "Cell–Free Synthesis Bioreactor", 1992 American Chemical Society, pp. 31–43.

Spirin et al., "A Continuous Cell–Free Translation System Capable of Producing Polypeptides in High Yield", vol. 242, pp. 1162–1164, 1988.

Suzuki, "Effects of Concentration of KCI, Magnesium Acetate and Spermine on the Ratio of a to B Globin Chains Synthesized", J. Biochem., 82, 251–260 (1997).

Volyanik et al., "Synthesis of Preparative Amour of Biologically Active Interleukin–6 Using a Conuous–Flow Cell–Free Translation System", Analytical Biochemistry 214, 289–294 (1993).

Yamamoto et al., "Hollow Fiber Reactor For Continuous Flow Cell–Free Protein Production", vol. 29. No. 6. 1996 (pp. 1047–1050).

Zubay et al., "In Vitro Synthesis Of Protein in Microbial Systems", 1973, p. 267–287.

Roche Molecular Biochemicals, "Linked in vitro SP6/T7–Transcription/Translation Kit–radioactive", 14 pgs.

(Image), Single Tube Protein System 3, Copyright 1998 by Novagen, Inc., (12 pgs.).

US 6,783,957 B1

METHOD FOR SYNTHESIS OF POLYPEPTIDES IN CELL-FREE SYSTEMS

FIELD OF THE INVENTION

The invention pertains to the field of molecular biology, in particular to synthesis of proteins and polypeptides in cell-free systems prepared from prokaryotic and eukaryotic cells.

BACKGROUND

Synthesis of polypeptides and proteins in cell-free translation systems of the first generation (U.S. Pat. No. 4,668,624, Roberts, 1978) was performed in a static (batch) mode where the reaction mixture is in static conditions with constant $Mg^{2+}$, $K^+$ and NTP concentrations, constant pH and temperature. To this end, extracts and lysates of prokaryotic (Zubay, 1973) and eukaryotic cells (Roberts and Paterson, 1973; Pelham and Jackson, 1976) were prepared, and natural and synthesized mRNAs were used (U.S. Pat. No. 4,937,190, Palmberg, 1990).

Rapid development of biotechnology has called for alternative methods that would increase the yield of synthesized proteins. The design of more productive translation systems in which the concentration of basic components is maintained constant during the synthesis is one direction of efforts aimed at improvement of the existing methods. In the second generation systems (Spirin et al., 1988), a continuous flow of low weight substrates included in the feeding solution (CFCF mode) into the reactor volume and removal of target polypetides and low molecular weight products inhibiting the cell-free system increases the time of its operation and raises the yield of the desired protein as compared to the classic system of synthesis in static (batch) conditions. Numerous studies have been focused on optimization of the conditions for CFCF protein synthesis (Baranov, 1989; Ryabova et al., 1989; Takanori et al., 1991; Spirin, 1992, Baranov and Spirin, 1993; Volyanik et al., 1993; Erdman et al., 1994; Kim and Choi, 1996; Yamamoto, 1996; Ryabova et al., 1998, EP Patent 0312617; Alakhov et al., 1993, EP Patent 0401369, Baranov et al., 1995, U.S. Pat. No. 5,434,079; Mozayeni, 1995; JP Patent 7075592, Shimizu, 1995; JP Patent 7031494, Sakurai, 1995; JP Patent 5076381, Sato, 1995; EP Patent 0593757, Baranov et al., 1997; U.S. Pat. No. 5,593,856, Choi et al., 1997).

U.S. Pat. No. 5,478,730 (Alakhov et al., 1995) describes a method in which the synthesis in cell-free translation systems is based on continuous exchange (CECF mode) of the feeding solution components with the component of the reaction mixture via a semipermeable barrier by a diffusion process. The results obtained by many authors (Davis et al., 1996; Kim and Choi, 1996; U.S. Pat. No. 5,593,856, Choi, 1997; JP Patent 10080295, Yamane, 1998) demonstrate a significant increase in the yield of the target polypeptide upon continuous exchange, as compared to the static (batch) mode of operation.

In addition to improvement of the components of the translation system, efforts were made to improve methods for preparation of mRNA in transcription systems including RNA polymerase and DNA. In these systems, preparation of mRNA depends on the concentration of RNA polymerase and DNA, as well as on the concentration of $Mg^{2+}$, $K^+$ and NTP and other ionic conditions (Kern and Davis, 1997). The cost of components of the in vitro transcription including RNA polymerase, DNA and NTP is very high. Therefore it is necessary to analyze conditions of transcription and optimize the process of mRNA preparation (Gurevich et al., 1991).

There are methods for synthesis of polypeptides in a CFCF mode in prokaryotic cell-free systems in conditions of a coupled transcription-translation (Baranov et al., 1989; EP Patent 0401369, Baranov et al., 1995; Ryabova et al., 1998) and the process was patented where transcription and translation occur in eukaryotic cell-free systems in the same reaction volume (Spirin, 1992; Baranov and Spirin, 1993; EP Patent 0593757, Baranov et al., 1997).

It is known (Craig et al., 1993) that translation and transcription conditions in eukaryotic cell-free systems differ and are determined largely by the concentrations of $Mg^{2+}$ and $K^+$. Therefore, two-stage (U.S. Pat. No. 5,665,563, Beckler, 1997; Operating Guide, Single Tube Protein™, Novagen Inc., 1998) or three-stage synthesis (Roberts and Paterson, 1973) is widely used in a static (batch) mode. At the first stage optimal conditions are achieved for mRNA transcription, then the mRNA is purified or immediately added to a new reaction mixture with conditions for translation. A one-stage synthesis of polypeptides in a transcription-translation eukaryotic cell-free systems is known (U.S. Pat. No. 5,34,637, Thompson et al., 1994; Operation Guide, Linked in vitro SP6/T7 Transcription/Translation Kit, Roche Diagnostics GmbH, 1998). The authors of the patent (U.S. Pat. No. 5,324,637, Thompson et al., 1994) used a known principle of optimization of $Mg^{2+}$ concentration in the reaction mixture. By adding $Mg^{2+}$ to the reaction mixture prior to the synthesis, they achieved such a concentration of $Mg^{2+}$ in the reaction system which is intermediate between the transcription optimum and the translation optimum. Further studies showed that such optimization has no advantages over the two-stage or three-stage procedures. The study of Laios et al. (1998) demonstrates that optimization of separate stages of transcription and translation is from 2 to 6 times more efficient than that of a coupled process. On the other hand, optimization of the selection of $Mg^{2+}$ concentrations is based on a preliminary measurement of the magnesium concentration in the lysate or in the reaction volume which devalues the principle of the one-stage procedure.

European Patent 0593 757 (Baranov et al., 1997) describes the possibility to perform continuous CFCF synthesis of polypeptides in eukaryotic cell-free transcription-translation systems for 20 hours. During the synthesis, the $Mg^{2+}$ concentration in the reaction mixture is maintained at the required level due to the constant concentration of $Mg^{2+}$ in the feeding solution. Since ribonuclease activity in the reaction volume is low and the mRNA templates retain their activity for a prolonged time, the reaction system works with both the earlier and newly synthesized mRNA templates and synthesizes a target product due to the constant $Mg^{2+}$ concentration. For a more productive synthesis, the transcription system should synthesize an adequate amount of mRNA. Therefore a large quantity of expensive polymerase SP6 or T7 (30,000 units) is required. It is mentioned in the text of the patent that optimal conditions of synthesis should be chosen in each individual case. To make an appropriate choice, it is necessary to perform a series of syntheses in a batch volume at different $Mg^{2+}$ concentrations and determine its optimal value for the given polypeptide. Optimization of the process is time consuming and rather expensive.

There are many devices in which the continuous exchange mode (CECF) is maintained due to a diffusion process. The device, in the form of a dialysis container for synthesis of polypeptides in a cell-free system, was first described in U.S. Pat. No. 5,478,730 (Alakhov et al., 1995). Promega Corp. (Davis et al., 1996) made a comparative analysis of syntheses (in a static (batch) mode and at a continuous exchange mode) during coupled transcription-translation in a *E. coli* prokaryotic cell-free system. To this end, the authors used "DispoDialyser" instruments manufactured by Spectrum Medical Industr. (U.S. Pat. No. 5,324,428, Flaherty, 1994) and "Slidealyzer" dialysers manufactured by Pierce Chemical Comp. (U.S. Pat. No. 5,503,741, Clark. 1996).

For the synthesis of polypeptides upon coupled transcription-translation in a preliminarily concentrated prokaryotic cell-free system of *E. coli*, Kim and Choi (1996) used a dialysis membrane fixed at the bottom of a cylinder.

Yamamoto (1996) constructed a dialyser in which the membrane is made from hollow fibers. The feeding solution passes through the hollow fibers. Due to diffusion, the components of the reaction mixture exchange with those of the feeding solution.

In the device designed by Yamane (JP Patent 100809295, Yamane, 1998), the membrane is used to maintain constant conditions of synthesis due to diffusion of low molecular substrates of the feeding solution circulating along the dialysis membrane.

U.S. Pat. No. 5,478,730 (Alakhov et al., 1995) is most close to the dialyser operating in a continuous exchange mode. The authors of the patent give a detailed description of requirements for the porous barrier made either of a dialysis membrane, flat membrane or hollow fibers, which can be composed in multi-layered structures.

Many devices whose operation is based on a continuous flow (CFCF) mode have been developed. They differ from each other by the formation of the feeding solution flows and the modes of removal of products of synthesis and metabolism inhibiting operation of the system.

The use of one ultrafiltration membrane in a flow-type reactor is described in many papers (Spirin et al., 1988, 1992; Takanori et al., 1991; Spirin, 1992; Volyanik et al., 1993; Kim and Choi, 1996; Ryabova et al., 1998). A disadvantage of this method is that the incoming flow of the feeding solution is equal to the volume of the outcoming flow of low molecular and high molecular components resulting in fast closing of the pores of the ultrafiltration membrane.

In 1990 Fischer et al. (DE Patent 3914956) proposed a method using a multifold pulse supply of the feeding solution to the reaction volume. To this end, N cycles are formed to provide positive and negative pressure in the reaction volume. Upon formation of positive pressure, the inhibiting products are removed from the reaction volume via the porous barrier and mixed with the feeding solution. At negative pressure, part of the inhibiting products are returned to the reaction volume via the porous barrier together with another portion of the feeding solution. Moreover, high molecular weight components of the cell-free system required for a prolonged synthesis are intensely washed out from the reaction mixture.

In 1995 Mozayeny (U.S. Pat. No. 5,434,079) proposed a device with improved removal of high molecular weight products due to an increased area of the ultrafiltration membrane. During synthesis the components of the cell-free system are removed together with the target product via the large area of two parallel membranes with pore sizes from 70 to 100 kD, which limits the time of the synthesis.

The devices proposed herein are most close to the device described in U.S. Pat. No. 5,478,730 (Alakhov et al., 1995) with one or two porous barriers. The barriers can be made of flat membranes or hollow fibers.

Generally, the prior art describes methods and devices developed for maintaining constant conditions during the synthesis. Constant conditions are provided both by removal from the reaction volume the low molecular weight products which inhibit operation of the cell-free system and by supplying into the reaction volume some components which maintain the synthesis. The synthesis is maintained by the same concentrations of $Mg^{2+}$, $K^+$ and NTP and other components both in the reaction mixture and in the feeding solution. The authors of the prior art patent use a well known principle of optimization. Optimization of the process is time consuming and rather expensive.

SUMMARY OF THE INVENTION

The object of the present invention is to provide a method that will allow the synthesis of a target polypeptide in prokaryotic and eukaryotic cell-free systems. The invention is based on modification of methods of synthesis in a continuous flow (CFCF) mode or a continuous exchange (CECF) mode. In these modes, during the synthesis parallel to input into the reaction mixture of components maintaining the synthesis and output from the reaction mixture of low molecular weight components inhibiting the synthesis, concentrations of at least one of the selected components determining the productivity of the synthesis ($Mg^{2+}$, $K^+$, NTP, polyamines or their combinations) are continuously changed from the upper to the lower limit of the determined range.

LIST OF FIGURES

The invention is illustrated by the following figures.

Figure 4:
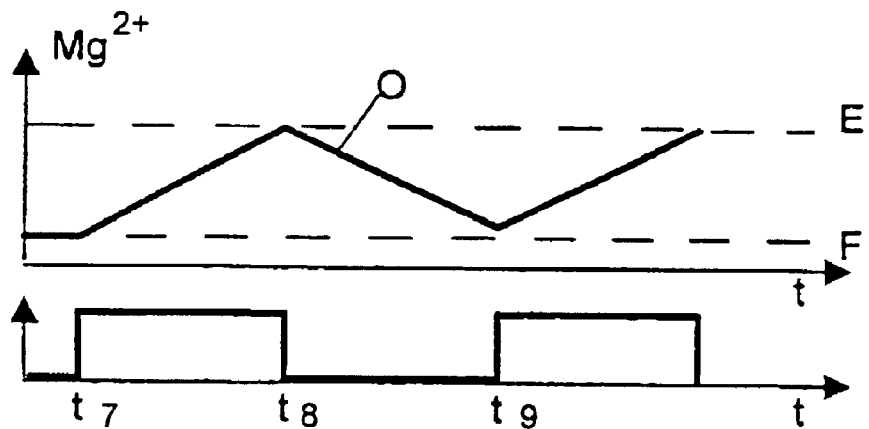

FIG. 4 demonstrates a diagram of recurrent changes in $Mg^{2+}$ concentrations according to the linear gradient shape.

Figure 5:
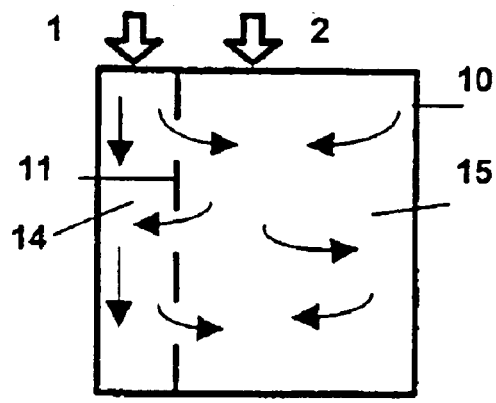

FIG. 5 shows a scheme of a reactor with one porous barrier.

Figure 6:
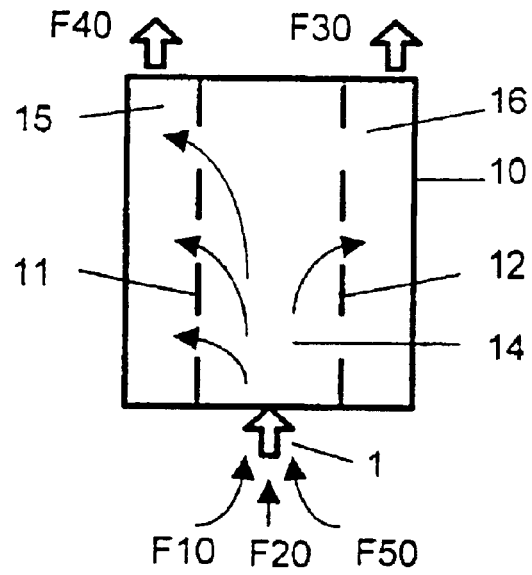

FIG. 6 shows a scheme of a reactor module and directions of flows formed in the mode of branched output of high molecular weight and low molecular weight fractions (CFCF-BF).

Figure 7:
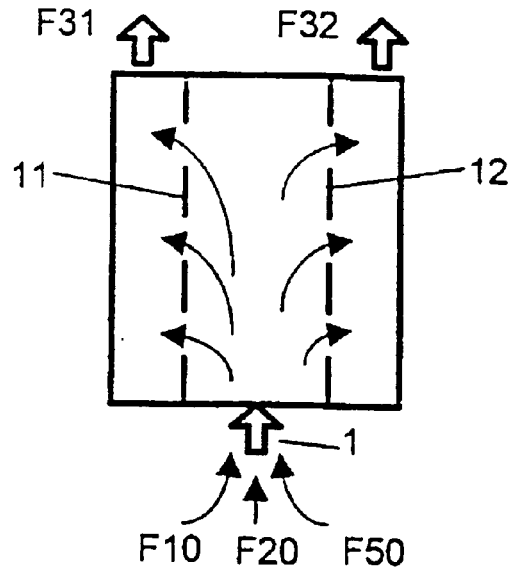

FIG. 7 represents a scheme of branched flows when the target product is removed from the zone of synthesis (CFCF-RP).

Figure 8:
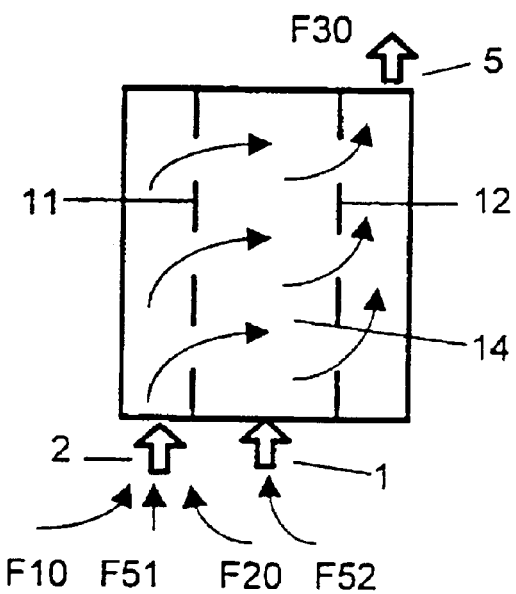

FIG. 8 shows a scheme of a reactor module and flow branching when the first porous barer plays the role of a distributor of flows of the feeding solution and the additional mixture with the target product remaining in the zone of synthesis (CFCF-RP).

Figure 9:
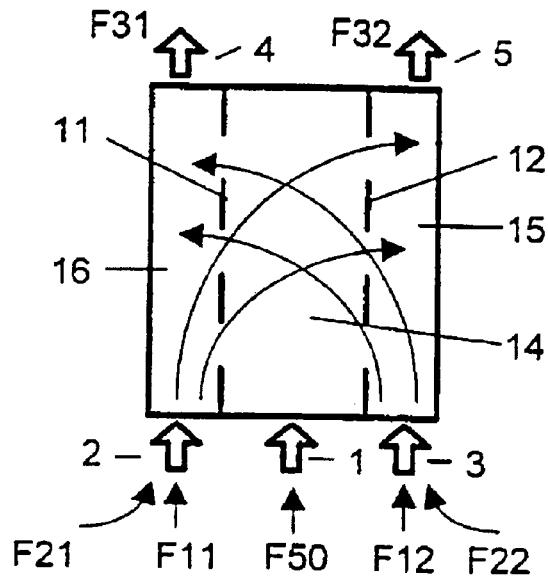

FIG. 9 represents a scheme of a reactor module and flow branching when directions of the feeding solution input are recurrently switched from the first porous barrier to the second one (CFCF-RF).

Figure 10:
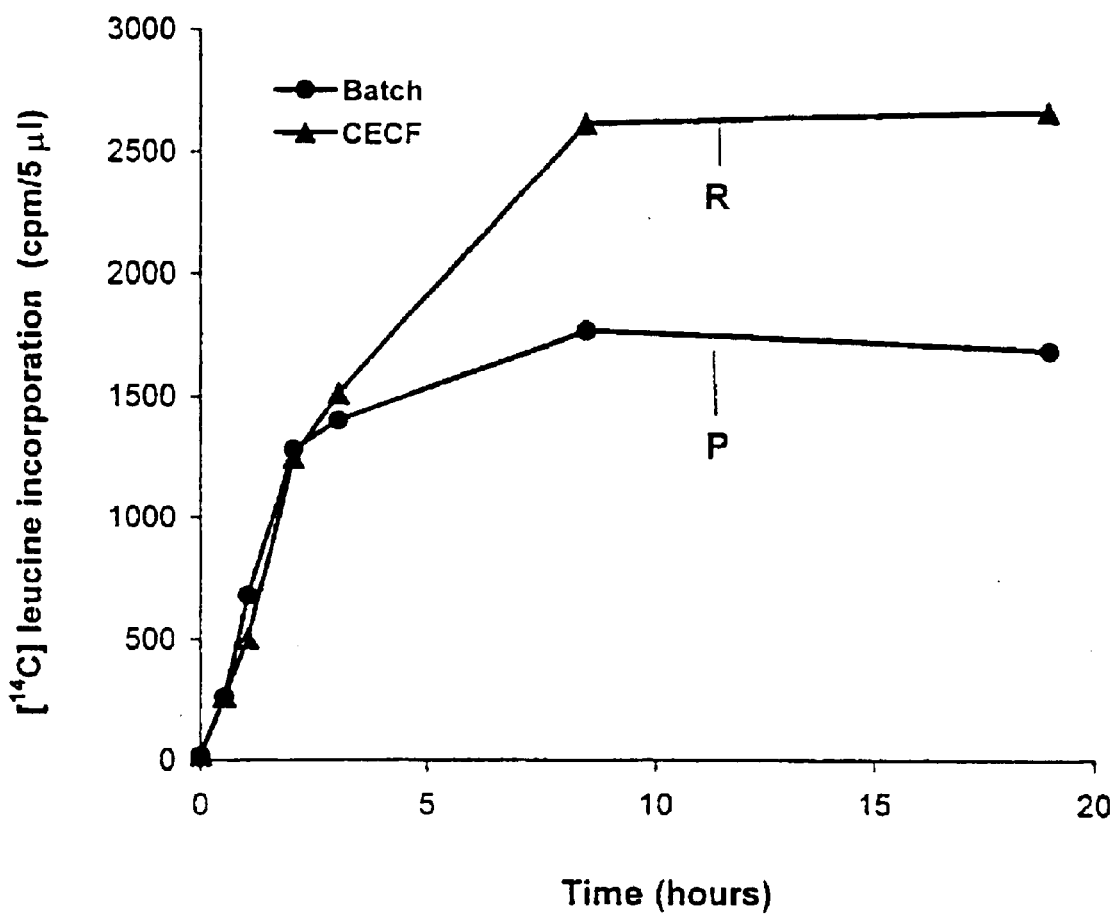

FIG. 10 shows the kinetics of CAT synthesis. Diagram P refers to the synthesis in a static (batch) mode. Diagram R demonstrates the kinetics of CAT synthesis upon translation in the CECF mode.

Figure 11:
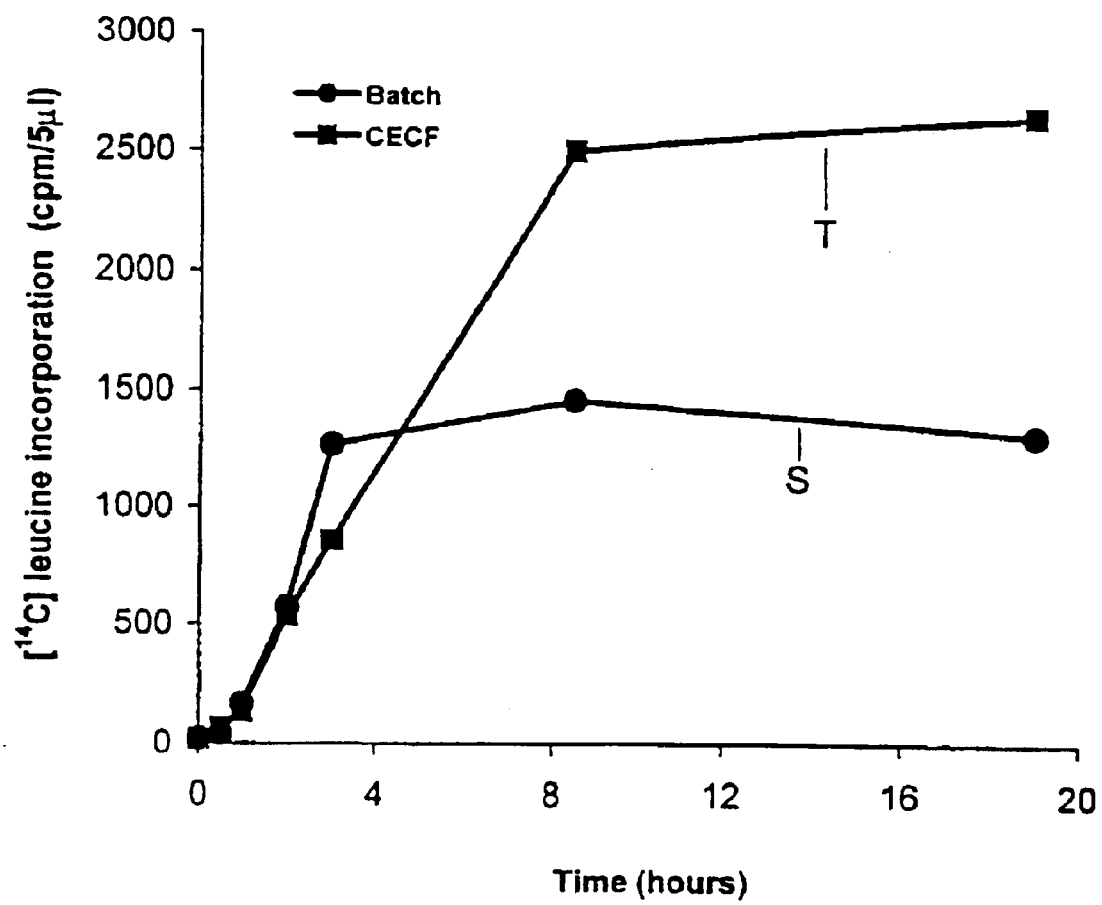

FIG. 11 shows the kinetics of CAT synthesis in the combined transcription-translation system. Diagram S represents synthesis in the static (batch) mode. Diagram T represents the kinetics of CAT synthesis upon transcription-translation in the CECF mode.

Figure 12:
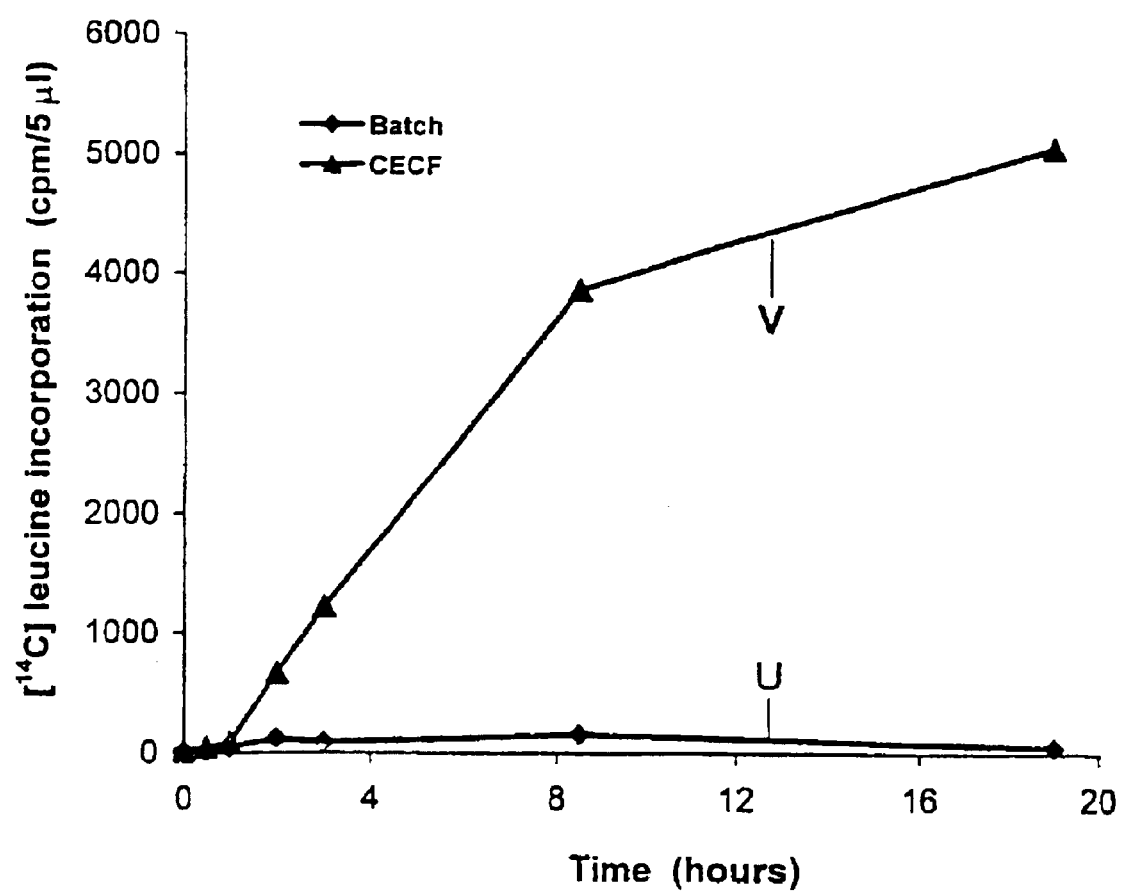

FIG. 12 shows the kinetics of CAT synthesis in the combined transcription-translation system with changing concentrations of $Mg^{2+}$ and NTP in the reaction mixture during the synthesis. Diagram U represents synthesis in the (static) batch mode. Diagram V represents the kinetics of CAT synthesis upon transcription-translation in the CECF mode.

Figure 13:
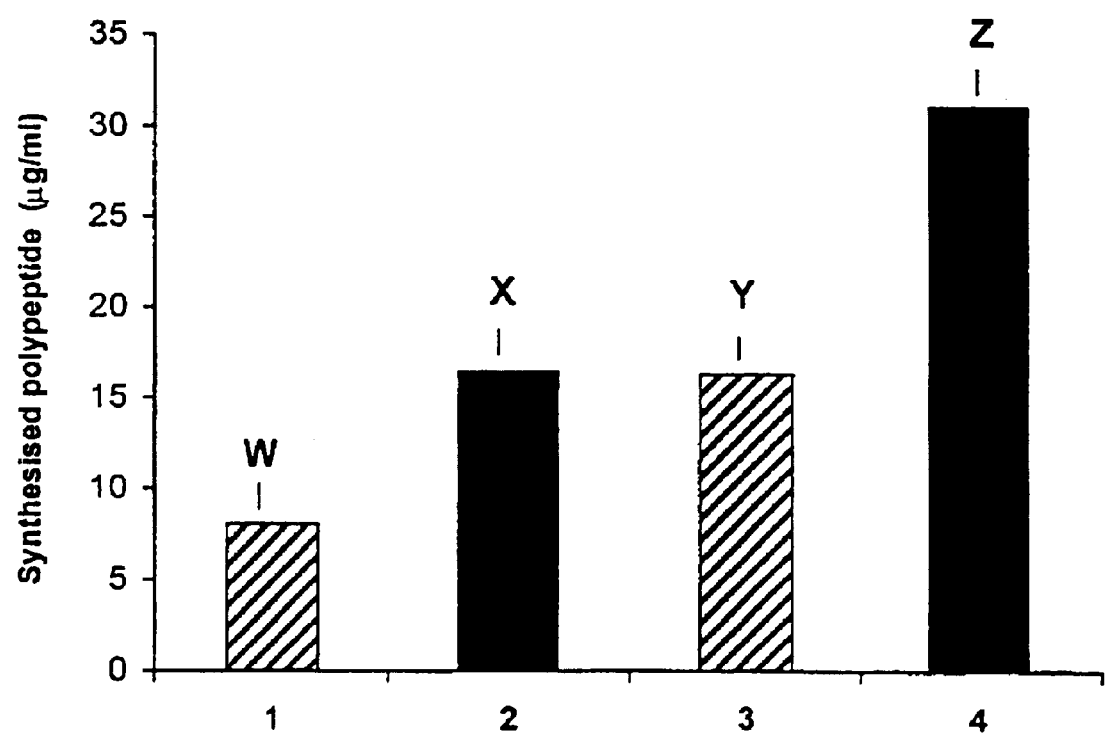

FIG. 13 shows a diagram which compares the results of four experiments on the synthesis of the target CAT polypeptide.

DESIGNATIONS USED IN THE FIGURES

F10, F11, F12 are the feeding solution flows.

F20, F21, F22 are the additional mixture flows.

F30, F31, F32 are flows of low molecular weight products of the reaction mixture.

F40 is the flow of high molecular weight products of the reaction mixture.

F50, F51, RF52 are flows of high molecular weight components maintaining the synthesis.

Positions 1 through 9 designate inlets and outlets of the reactor.

Positions 10 through 19 designate the reactor elements.

Abbreviations Used in the Text $Mg^{2+}$, magnesium ions added as a magnesium salt;

$K^+$, potassium ions added as a potassium salt.

DESCRIPTION OF SPECIFIC EMBODIMENTS

1. Stages of the Synthesis

The synthesis consists of the following stages.
1. The reaction mixture is prepared using a cell lysate or cell extract.
2. The feeding solution and the additional mixture, which includes at least one of the selected components determining the productivity of the synthesis are prepared.
3. The mode of reactor operation is determined, the type of the reactor module is selected with a given number and types of porous barriers. The volume ratio of the reaction mixture and the feeding solution or the rate of the feeding solution flow via the reaction volume are determined.
4. The device for the synthesis including at least one reactor module is assembled.
5. The reaction mixture and the feeding solution are supplied to the corresponding zones of the reactor module separated by at least one porous barrier.
6. The additional mixture is supplied to the reaction mixture or to part of the feeding solution prior to or during the synthesis.
7. In the course of the synthesis, the additional mixture is introduced once, recurrently or continuously, depending on the mode of operation.
8. In the mode of preparative synthesis, the required high molecular weight components are supplied to the reaction mixture once, recurrently or continuously.
9. The synthesized product is collected from the reaction mixture either at the end of synthesis or during the synthesis.
10. When the product is collected during the synthesis, it is analyzed and the conditions determining the system productivity are corrected.

2. Preparation of Reaction Mixtures

Cell-free systems are prepared using cell lysates and cell extracts. They include all components necessary for protein synthesis as well as regeneration system, NTP, a buffer and salts, and amino acids.

A great variety of types of cell-free systems are known for synthesis of polypeptides (U.S. Pat. No. 5,807,717, Joyce, 1998). They are prepared from archeaebacteria (Halobacterium, Thermoproteus, Methanococcus, Sulfolobus, etc.), eubacteria (Pseudonomas, Agrobacterium, etc.) and eukaryotic cells (rabbit reticulocytes, wheat germ, HeLa, mouse liver, etc.). Conditions described herein are most close to those of translation systems and transcription-translation systems prepared from prokaryotic E. coli extracts (Zubay, 1973), eukaryotic wheat germ extracts (Roberts and Paterson, 1973) and extracts prepared from rabbit reticulocytes (Pelham and Jackson, 1976).

One of the components of the transcription-translation cell-free system should be a DNA-dependent RNA-polymerase that synthsizes mRNA. It is selected from E. coli RNA polymerases or bacteriophage RNA pclymerases. In this invention, we analyze but do not restrict to the use of polymerases T1, T3, T5, T7, SP6, A16, PHL1, PHL11 in such systems. The most suitable are polymerases T7 and SP6 polymerases.

3. Conditions of Synthesis

It is known that in prokaryotic and eukaryotic cell-free systems conditions of synthesis differ. The productivity of synthesis depends on whether concentrations of such components of a cell-free system as $Mg^{2+}$, $K^+$ and NTP are within the optimal range and by what value they are changed during synthesis. The range of concentrations at which the synthesis is optimal is rather narrow. Any change in temperature, pH, initial concentrations of components during synthesis forces the cell-free system leave the mode of optimal synthesis, which results in a decreased yield of the synthesized product. For all cell-free systems, optimization means that the NTP value is a priori determined and such ranges of $Mg^{2+}$ and $K^+$ concentrations are selected in which the synthesis is most productive.

This leads to a great scatter of "optimal" magnesium concentrations given in different patents. For example, as mentioned in Promega's patent (U.S. Pat. No. 5,324,637, Thompson et al., 1994), for polypeptide synthesis in a transcription-translation system with a reticulocyte lysate, optimal magnesium concentrations in the reaction mixture vary from 2.5 to 3.5 mM. However, as given in the other patent (U.S. Pat. No. 5,807,717, Joyce, 1998), this range is 6.0–10.0 mM $Mg^{2+}$ for polypeptide synthesis in the same system with the reticulocyte lysate produced by Promega.

It is known (Pokrovskaya, 1994) that with the use of SP6, T7 and T3 polymerases optimal transcription takes place when $Mg^{2+}$ concentration varied from 16 to 36 mM. Concentrations of NTP determine largely initiation of transcription (Guajardo et at., 1998), and $Mg^{2+}$ concentrations should exceed the total concentrations of NTP (Gurevich et al., 1991; Kern and Davis, 1997) for an efficient action of the T7 polymerase. At the same time, for optimal translation of mRNA in cell-free systems with a reticulocyte lysate prepared by a standard technique (Pelham and Jackson, 1976; Suzuki, 1977; Merrick, 1983), magnesium concentrations may vary from 1.0 to 3.0 mM of $Mg^{2+}$ added to the reaction mixture.

In this invention, contradictions appearing in determination of $Mg^{2+}$ and $K^+$ concentrations, which provide the required level of both transcription and translation, are solved otherwise as compared to the known method when optimal concentrations of $Mg^{2+}$ and $K^+$ are determined by results of intermediate experiments. Herein this is done in the following way. During the synthesis, parallel to input to the reaction mixture of components maintaining the synthesis and output from the reaction mixture of low molecular weight components inhibiting the synthesis, concentrations of at least one of the selected components determining the productivity of the synthesis ($Mg^{2+}$, $K^+$, NTP, polyamines or their combinations) are continuously changed from the upper to the lower limit of the determined range.

The choice of the upper and lower limits of this range depends on the mode of synthesis, parameters of the cell-free extract, conditions of both the reaction mixture and the feeding solution. If $Mg^{2+}$ is taken as one of the selected components, $Mg^{2+}$ concentrations (for various modes including transcription, transcription-translation, translation) range from 0.25 to 50 mM of added $Mg^{2+}$. When one of the components of a cell-free system is DNA-dependent RNA polymerase, in the mode of RNA transcription the upper and lower limits of a given range of changes in $Mg^{2+}$ concentrations should be from 2 to 50 mM of added $Mg^{2+}$. If protein synthesis proceeds in conditions of transcription-translation, these limits should be from 2 to 25 mM of added $Mg^{2+}$. If protein synthesis proceeds in conditions of translation, the upper and lower limits of a certain range of changes in $Mg^{2+}$ concentrations should be 0.25 and 25 mM of added $Mg^{2+}$, correspondingly. It is possible that these limits are chosen so that during synthesis, conditions of synthesis change together with the mode of synthesis (i.e. predominant transcription switches to transcription-translation or predominant translation). The previous example involves ranges of concentrations of only one of the selected components ($Mg^{2+}$) required for synthesis. The width of the selected ranges and their upper and lower limits are determined taking into account conditions of synthesis in prokaryotic and eukaryotic cell-free systems.

The other goal of this invention is to lower the cost of synthesis of a certain amount of polypeptide in eukaryotic cell-free systems. In the known methods, synthesis is performed at a high concentration of expensive T7 polymerase at a continuous flow via the reaction volume of expensive components of the feeding solution such as NTP and amino acids (European Pat. No. 0,593,757, Baranov et al., 1997). In this invention, the productivity of synthesis in transcription-translation systems increases, since high concentrations of $Mg^{2+}$ and NTP introduced to the reaction mixture at the beginning of synthesis decrease the amount of abortive mRNA, which in its turn reduces the expenditure of ATP, GTP and amino acids during translation.

Some examples included in this invention which concern the principle of a continuous flow of the feeding solution via the reaction volume (CFCF) are aimed at lowering the cost of preparative synthesis of target polypeptides. The feeding solution flow and concentrations of selected components can be readily controlled by changing the rate and direction of the flow with a pump. Other examples demonstrate the use of the continuous exchange (CECF) and the possibility to increase productivity of the synthesis due to continuous changes in the concentration of at least one of the selected components. As known, the rate of exchange of low molecular weight components included in the reaction mixture and in the feeding solution via the dialysis membrane depends on many conditions (membrane area, pore size, etc.). This restricts the choice of modes of synthesis and the choice of upper and lower limits of the range for changing the concentrations of selected components. For example, in a CECF mode, it is more preferable to perform synthesis in separate modes (transcription, translation, transcription-translation) or in a combination of two modes (e.g. transcription and transcription-translation or transcription-translation and translation), or in a combination of three modes (e.g. transcription, transcription-translation and translation). This is caused by the fact that due a rather tow rate, the exchange takes a lot of time and cannot correspond to the rate required for input of low molecular weight components necessary for the synthesis and removal of low molecular weight products inhibiting the operation of the system.

Figure 1:
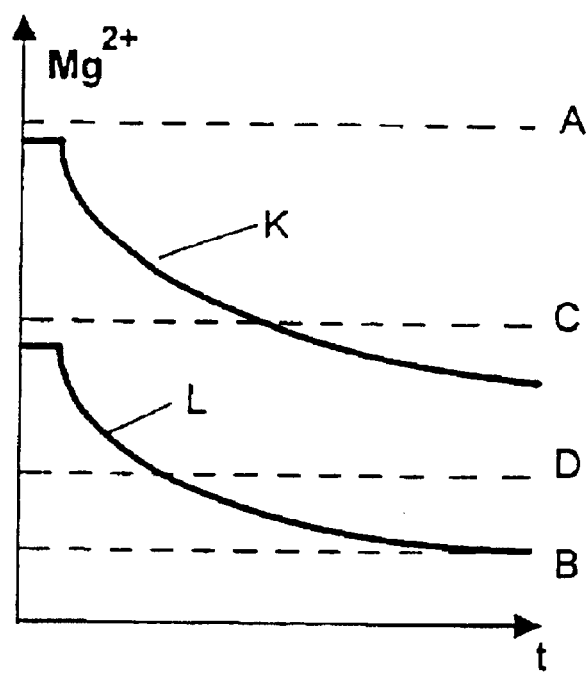
FIG. 1 shows diagrams of changes in $Mg^{2+}$ concentrations upon synthesis of mRNA and synthesis of polypeptides in a cell-free system operating in a continuous exchange mode (CECF).

FIG. 1 shows two examples of changes of $Mg^{2+}$ concentrations in the reaction mixture for different modes of synthesis. One example demonstrates the case when it is necessary to carry out synthesis of a large amount of mRNA. As seen from the diagram (K), changes of concentrations of selected components from the upper level (A) to level (C) are in the range within which conditions of predominant transcription and mRNA synthesis are formed in the reaction mixture due to high concentrations of $Mg^{2+}$ and NTP. Here the initial concentration of $Mg^{2+}$ should not exceed that of NTP by more than 10 mM. The following decrease in the concentration of $Mg^{2+}$ and NTP is caused by the fact that the system adjusts $Mg^{2+}$ and NTP concentrations to the corresponding values of the upper limit of the transcription-translation zone (C-D zone). The other example (diagram L) demonstrates the case when the upper limit of $Mg^{2+}$ and NTP concentrations corresponds to the upper limit of the transcription-translation zone (C-D zone) and the lower limit coincides with the lower limit of the translation zone (D-B zone). In this case, conditions of the reaction mixture change from predominantly transcriptional to predominantly translational during the synthesis. Parameters of the porous barrier (pore size, membrane area, membrane type) and the rate of the feeding solution flow over the surface of the porous barrier should be chosen with account for the diffusion rate and exchange of low molecular weight components of the feeding solution and the reaction mixture, so that they would provide the required exchange rate and changing of the $Mg^{2+}$ and NTP concentrations during the synthesis. The choice of the upper and lower limits of the concentrations depends on the properties of the cell-free extract that can be prepared in different ways. The properties of the reaction mixture depend on the percentage of the extract and feeding solution contained in the mixture. Determination of the upper and lower limits, within which concentrations of the selected components are changed during the synthesis, allows to control the productivity of the cell-free system in different modes.

The continuous flow mode (CFCF) allows a rapid change of the rate and direction of the feeding solution flow via the reaction mixture. This permits to control the rate of changing the concentrations of selected components at various stages of the synthesis. During one run it is possible to choose different rates of the feeding solution flow via the reaction mixture. Therefore it becomes possible, during synthesis of polypeptides in a transcription-translation cell-free system, to adjust duration of individual stages at which parameters of the reaction mixture and concentrations of selected components correspond to those of predominant transcription, transcription-translation or translation. The choice of definite parameters within which concentrations of selected components can be changed depends on the aim of synthesis (synthesis of mRNA, or synthesis of a target polypeptide in the translation mode, or synthesis of a target polypeptide in the transcription-translation mode), selected conditions of synthesis and, first of all, properties of the cell extract, parameters of porous barriers (pore size, membrane area and membrane type), possibility to add expendable high molecular weight components. The upper limit of the allowable range of $Mg^{2+}$ concentrations (from which a working range is determined) cannot exceed 50 mM in CFCF transcription-translation systems with DNA-dependent RNA polymerase. The lower limit of $Mg^{2+}$ concentrations cannot be below 0.25 mM.

Figure 2:
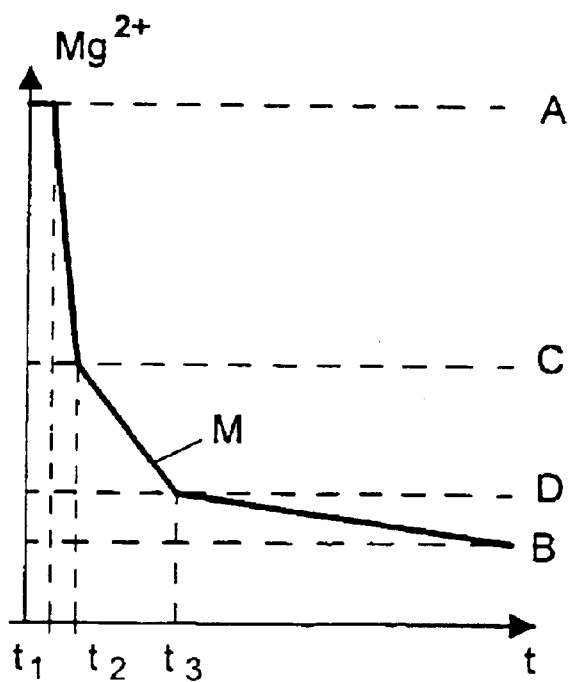
FIG. 2 shows a diagram of changes of $Mg^{2+}$ concentrations upon synthesis in a continuous flow mode (CFCF) when the conditions of synthesis are changed from predominantly transcriptional to predominantly translational.

FIG. 2 shows the dependence (M) of changes in $Mg^{2+}$ concentrations on the time of transcription-translation synthesis. Adjusting the rate of the feeding solution flow at the first stage of synthesis ($t_1$–$t_2$ period) it is possible to correct the amount of synthesized mRNA and prevent their overproduction. The high concentration of $Mg^{2+}$ and NTP at the beginning of the first period ($t_1$–$t_2$) decreases the required amount of expensive RNA polymerase, because mRNA synthesis proceeds with a lower yield of abortive mRNA. The ratio of $Mg^{2+}$ and NTP concentrations is selected so that at the first stage $Mg^{2+}$ concentration exceeds NTP concentration by a value of 5 to 10 mM, whereas at the third stage this excess of $Mg^{2+}$ over NTP would not be less than 0.5 mM.

Figure 3:
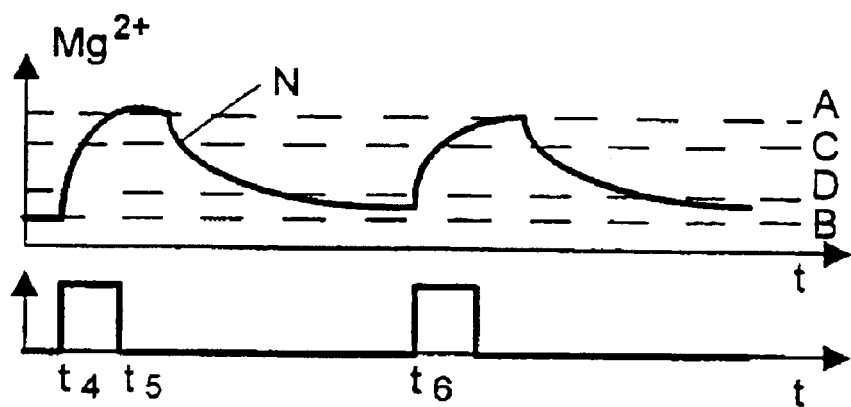
FIG. 3 shows a diagram of changes in $Mg^{2+}$ concentrations at a recurrent pulse input of the additional mixture to the reaction mixture.

Upon a prolonged synthesis in a CFCF mode, concentrations of selected components are changed from the upper to the lower limit once or recurrently. FIG. 3 shows a diagram (N) of changes in $Mg^{2+}$ and NTP concentrations at a recurrent pulse input of the additional mixture to the reaction mixture. The synthesis is divided in N steps with a step duration from $t_4$ to $t_6$. The additional mixture is introduced during the $t_4$–$t_5$ time. $Mg^{2+}$ and NTP concentrations increase, pass level C, and conditions of synthesis in the reaction system achieve zone A-C where predominant transcription of mRNA takes place. A decrease in $Mg^{2+}$ and NTP concentrations changes conditions of synthesis from transcription-translation (zone C-D) to predominant translation (zone D-B).

During preparative synthesis of target polypeptides not only low molecular weight components of the feeding solution are required for the prolonged synthesis. In this mode in addition to low molecular weight components, high molecular weight components are also introduced into the reaction mixture. These components are (I) a ribosomal fraction, (ii) a cell-free extract (S30, S100 and their modifications), (iii) polymerases, (iv) plasmids, (v) tRNA. With regard to the conditions of synthesis, high molecular weight components are introduced once, recurrently or continuously. It is preferable to introduce such components as polymerases and plasmids to the reaction mixture together with the input of the maximal concentration of $Mg^{2+}$ and NTP at the stage of transcription. The ribosomal fraction may be input upon translation.

FIG. 4 shows the diagram (O) of changes in $Mg^{2+}$ and NTP concentrations upon formation of linear gradient of these components. The process of linear gradient formation is well known and widely used, e.g., in liquid chromatography. It is advisable to use this mode for a preparative synthesis of the target polypeptide in the system of mRNA translation. In this mode, $Mg^{2+}$ and NTP concentrations, which are in the range of changes (zone E-F), should correspond to the range in which $Mg^{2+}$ and NTP concentrations are most close to the optimal translation of mRNA. The range of allowable $Mg^{2+}$ and NTP concentrations should be determined from the known types of extracts given in the literature or from technical descriptions of manufacturers. A decrease in the efficiency of translation in zones close to the limits of the E-F range is compensated by multiple iterations of the synthesis conditions via the optimum zone with a recurrent change in $Mg^{2+}$ and NTP concentrations proportional to the linear gradient shape. As in the above case, the whole synthesis is divided in N steps with each step duration varying from $t_7$ to $t_8$. At the first step, $t_7$–$t_8$, the additional mixture containing high $Mg^{2+}$ and NTP concentrations is mixed with the feeding solution, so that $Mg^{2+}$ and NTP concentrations in the total mixture increase. The total mixture is introduced to the reaction mixture and changes conditions of the synthesis. At the time, it maintains the synthesis and removes from the reaction volume low molecular weight components inhibiting the synthesis. With a change in the ratio of the mixed volumes and a decrease of input amount of the additional mixture relative to the feeding solution, $Mg^{2+}$ and NTP concentrations in the total mixture decrease. The decreased $Mg^{2+}$ and NTP concentrations pass the region of the E-F zone where the synthesis is maximal. Depending on conditions of the synthesis, excess high molecular weight components maintaining the synthesis are added to the reaction volume continuously or recurrently.

A similar mode can be used also for controlling the preparative transcription in order to obtain a sufficient amount of mRNA. The difference of the known methods for synthesis of mRNA in a batch mode and the methods with fed batch of transcription systems without removal of low molecular products (Kern and Davis, 1997) is as follows. (a) Due to removal of low molecular weight components inhibiting synthesis of mRNA, the process of synthesis is prolonged and the yield of mRNA increases. (b) Due to the choice of the lower limit of the range for $Mg^{2+}$ and NTP concentrations, it is possible to obtain mRNA in conditions that promote the next stage of translation of the synthesized mRNA without additional purification. (c) The use of high $Mg^{2+}$ concentrations (up to 50 mM) results in a decreased yield of abortive or incomplete mRNA molecules and lowers the consumption of expensive RNA polymerase.

4. Reactor Module

The above modes of operation can be realized by a proper choice of a design of the reaction module. Using porous barriers which are placed inside the reaction module, a reaction volume is formed as well as zones for both input of the feeding solution and additional mixture components, expendable high molecular weight components maintaining the synthesis, and output from the reaction module of low molecular weight components inhibiting the synthesis, and in some modes output of high molecular weight components including the target polypeptides.

In the simplest construction, the reaction volume is divided into two zones: (a) in a CECF mode, the volume is divided by a porous barrier in the zone with the reaction mixture and the zone with the feeding solution; (b) in a CFCF mode, the volume is divided by a porous barrier in the zone with the reaction mixture where the feeding solution is added, and the zone for removal of synthesized products (U.S. Pat. No. 5,478,730, Alakhov et al., 1995).

There are reactors in which three zones are formed (U.S. Pat. No. 5,135,853, Dzewulski et al., 1992; U.S. Pat. No. 5,478,730, Alakhov et al., 1995; DE Patent Appl. 19832160.0 A1, Bauer et al., 1998); a zone for the feeding solution input, a zone with the reaction mixture and a zone for output of sythesized products. Such a division is required for maintaining constant conditions of synthesis. In this invention, the productivity of synthesis should be supported, on the one hand, by a constant composition of amino acids and other components in the reaction mixture and, on the other hand, by active (in the CFCF mode) or passive (in the CECF mode) regulation of concentrations of selected components. These conditions determine the choice of a construction of reactors designed for operation in different modes. The construction of a reactor with two porous barriers forming three zones in the reactor volume is most widely used in different modes. The number of zones can be increased as required by the peculiarities of the reactor module.

The reaction mixture volume depends on conditions and purposes of synthesis. As known (U.S. Pat. No. 5,324,637, Thompson et al., 1994), for research purposes the synthesis is performed in microvolumes. Synthesis on a preparative scale (European Patent 0593757, Baranov et al., 1997) is performed in reactors whose volume varies from 500 µl to 1.0 ml. For research purposes, the minimal reaction volume should be from 50 to 500 µl. For preparative synthesis, one or several reaction modules with a volume from 500 µl to 10 ml are used. The number of reaction volumes in the reactor may vary from 1 to 10 depending on the types of reactor modules.

Three processes should proceed simultaneously in each point of the reaction volume: (a) input of the feeding solution, (2) output of low molecular weight products inhibiting the synthesis, and (3) a temporary change in the concentration of selected components determining the productivity of the synthesis. The most preferable is the reactor module in which various shapes of thin layers of the reaction mixture are formed. The layer thickness is chosen so that the continuous exchange of the reaction mixture and the feeding solution components or the feeding solution flow via the reaction mixture, as well as removal of low molecular weight products, inhibiting the synthesis, would proceed during the period when the synthesis does not drop below the allowable level. The reaction mixture can be placed to the volume of any shape formed between the surfaces of the porous barriers. With the use of hollow fibers, flat membranes or their combinations, the reaction volume can have the form of a cylinder or a thin flat sheet of 0.1 to 5.0 mm thickness. The internal volumes of the reaction system and the feeding solution can intermix either due to a closed loop circulation of the reaction mixture using a pump (U.S. Pat. No. 54,343,079, Mozayeni, 1995), due to shaking the reactor (U.S. Pat. No. 5,593,856, Choi, 1997) or due to the use of a magnetic stirrer (Kim and Choi, 1996). The reaction volume can be previously filled with different separators or extenders of an organic or inorganic nature. They can be of porous, layered or capillary materials chosen from the following: (a) filters from synthetic polymers or inorganic materials, (b) porous metals or their composition, (c) gel-like structures. Porous materials with pore sizes from 10 µm to 0.1 mm placed in the reaction mixture serve to increase the area on which molecules collide with each other and thus increase the rate of the synthesis reactions (Alberts et al., 1983). In addition to polymers, inorganic oxides and ceolytes (U.S. Pat. No. 5,593,856, Choi, 1997), these materials may comprise sorbents used in chromatography, including affinity sorbents (Maier et al., 1998) to isolate the target polypeptide from the reaction system. The use of any porous material for this purpose is restricted only by their chemical activity and possibility to inhibit the synthesis.

Porous barriers such as membranes, hollow fibers and other porous structures, ensure exchange of the feeding solution and reaction mixture components and play the role of distributors of the feeding solution flows via the reaction volume. There are no restrictions concerning the use in one reactor of porous barriers of different types (membranes, hollow fibers) and of different materials (solid or solid in a combination with gel). Porous barriers can be used both as one-layer or multi-layer constructs including those made of various materials.

The proposed herein variants of mutual positions of porous barriers can be modified using the existing knowledge of the art.

EXAMPLES OF REALIZATION OF THE INVENTION

Below are given examples of flow formation (the feeding solution, additional mixture or their combination) in reactor modules for an efficient synthesis in the continuous exchange (CECF) or continuous flow (CFCF) modes (example 1–example 5) and of synthesis of chloramphenicol acetyl transferase (CAT) in continuous exchange mode (example 6).

Example 1

FIG. 5 shows a scheme of reactor 10 with one porous barrier 11 which divides the reactor volume into two parts. In one part 14 restricted by the surface of porous barrier 11, is placed the reaction mixture introduced via inlet 1. In the other part 15, via inlet 2 the feeding solution is introduced which comes in contact with the surface of porous barrier 11. The porous barrier can have the form of a flat sheet or a cylinder. In the first case, dialysis or ultrafiltration membranes in the form of a disk, a square or a rectangle are used; in the second case, hollow fibers or dialysis containers. The reaction mixture is incubated at a temperature from 20 to 40° C. The temperature range preferable for wheat germ extract is 20–26° C., for reticulocyte lysate it is 24–38° C., and for E.coli extract it is 20–38° C. Tangential flows which move along the internal and external surfaces of the membrane are formed to intensify the exchange of the feeding solution and the reaction mixture. For the CECF mode, such porous barriers are chosen which would allow removal of only low molecular weight components from the reaction volume (when pore sizes do not exceed 30 kD) or simultaneous removal of low and high molecular weight components (when pore sizes vary from 30 to 100 kD). Inlets 1 and 2 of the reactor module can be closed hermetically or open during synthesis with the same pressure being maintained in both parts of the reaction volume. This permits to add substrates, which maintain the synthesis, to the reaction mixture or to the feeding solution and also to change the concentration of selected components independently of the diffusion. Before the synthesis, the volume ratio of the reaction mixture and the feeding solution is chosen to be from 1/5 to 1/100, and types of the reaction module are selected to correspond to this ratio, pore size and area of the dialysis membrane.

Description of the use of the proposed method for synthesis in the continuous exchange mode (CFCF) is given below.

For analytical purposes, synthesis of polypeptides is performed in microreactors with a reaction volume no smaller than 50 µl. Synthesis of preparative amounts of polypeptides imposes special requirements to the mode of synthesis and design of the reactor. Below are given variants which can be realized with a one-channel and multichannel reactors including those with branched flows inside the reactor volume. Variants of porous barriers, their parameters and thickness of the reaction mixture layer are mostly analogous to those described above. Reactors used in a flow mode should ensure (1) input of the feeding solution containing low molecular weight components to the reaction volume and (2) input of high molecular weight components directly to the reaction volume or via a porous barrier. The porous barrier plays the role of a distributor of flows with pore sizes not exceeding 5000 kD which ensure free penetration of most components of the S30 extract, excluding ribosomes and complexes formed around it. The number of possible constructions of reactors that can be designed using the existing knowledge is rather great, and the prior art does not restrict the range of other variants.

Example 2

Synthesis in the mode of a continuous input of the feeding solution with branched flows of output fractions of high and low molecular weight components (CFCF-BF) provides a possibility to concentrate the synthesized polypeptide inside the reaction mixture due to independent regulation of output flows. FIG. 6 shows a scheme of the reactor and directions of flows formed at a branched output of high molecular weight fraction F40 and low molecular weight fraction F30. The reactor has a housing 10, two porous barriers 11 and 12 which form reaction volume 14 located between internal surfaces of porous barriers, and two zones 15 and 16 for input/output of liquid circuits which contact the external surface of the porous barriers. The reaction mixture is input to the reaction mixture via inlet 1. To the same inlet are supplied (a) feeding mixture F10, (b) additional mixture F20, (c) fraction of high molecular weight components F50. The feeding mixture is supplied to inlet 1 continuously or recurrently. Depending on conditions of synthesis, additional mixture F20 and fraction of high molecular weight components F50 are supplied to the reaction mixture once, recurrently or continuously. Fraction of high molecular weight components F50 is input to the reaction volume independently of feeding solution F10, or high molecular weight components are preliminarily mixed with the feeding solution. Synthesis may be performed without input of fraction F50. Prior to its beginning, ratios of the volumes of fractions of the feeding solution, the additional mixture and the high molecular weight fraction to those of the reaction mixture and the flow rate of these fractions via the reaction volume are determined. Pore sizes of the first porous barrier 11 are selected, taking into account the molecular weight and dimensions of the target polypeptide, in the range from 30 to 100 kD; pore sizes of the second porous barrier 12 are taken not to exceed 30 kD. With regard to the selected mode of synthesis, the ratio of volumes passing via the first and second barriers is taken to be from 1/10 to 1/100.

Example 3

FIG. 7 shows a scheme of flows of a reactor where the first and second barriers have the same or different pore size not exceeding 30 kD. In this case, synthesis proceeds without removal of high molecular weight fraction F40 and the target product from the zone of synthesis (CFCF-RP), and flows F31 and F32 contain only low molecular weight components. This mode is used when the synthesized product exceeds 80–100 kD or when accumulation of the synthesized polypeptide in the reaction volume does not inhibit the synthesis. Modes of input of the feeding solution, the additional mixture and the fraction with high molecular weight components are similar to the CFCF-BF mode.

Example 4

Porous barriers can be used as distributors of the feeding solution and additional mixture flows when the volume, to which the reaction mixture is introduced, is filled with porous materials and mixing of the reaction volume is impaired or impossible.

FIG. 8 shows a scheme of the reactor module and the flow direction in a CFCF-RP mode when the first porous barrier plays the role of a distributor of flows of feeding solution F10 and additional mixture F20. Pore sizes of the first porous barrier 11 should not exceed 5000 kD. This permits to input part of the high molecular weight fraction F51 via the first porous barrier, if dimensions of the components included in this fraction are smaller than the pore size of the first barrier. Such components are tRNA, enzymes and others. When required, ribosomal fraction F52 is input to reaction volume 14 directly via liquid inlet 1. Pore sizes of the second porous barrier should not exceed 30 kD. The flow of low molecular weight components F30, inhibiting the system operation, is removed via outlet 5.

Example 5

FIG. 9 represents a scheme of flows for the CFCF-RF mode when the direction of the feeding solution supply via the first and second porous barriers is recurrently altered. In this mode designated for a prolonged synthesis of polypeptides, alteration of the direction of the feeding solution supply provides clearing the pores of the first 11 and second 12 porous barriers. The synthesis is performed either without removal of high molecular weight products from the reactor (pore sizes of the first and second barriers are taken to be the same and do not exceed 30 kD), or with removal of part of the synthesized product from the reaction volume (pore size of the first porous barrier should not exceed 100 kD, and that of the second porous barrier should not exceed 30 kD). The flow of high molecular weight components F50 is supplied to the reaction volume via inlet 1. N steps of the input of the feeding solution and the additional mixture are formed during synthesis. Each step is divided into two periods. During the first period, containers with the feeding solution and the additional mixture are connected to inlet 2 using liquid valves. The flows of the feeding solution F11 and the additional mixture F21 are input to zone 16 formed by the surface of the first porous barrier 11. Via pores of the first porous barrier, the feeding solution and the additional mixtures are supplied to the zone of synthesis 14 of the reactor. Via pores of the second porous barrier 12 low molecular weight components are removed from the zone of synthesis to zone 15, and then flow 32 is formed which is removed from the reactor via outlet 5. After termination of the first period, the valves are switched and containers with the feeding solution and the additional mixture are connected to inlet 3 which is linked to zone 15 formed by the second porous barrier 12. Flows F12, F22 penetrate via the second porous barrier to the reaction mixture and at the same time clear the pores of the second barrier which have closed during the first step of the synthesis. Low molecular weight components leave the reaction volume via the first porous barrier. They form flow F31 which is removed from the reactor via outlet 4. By adjusting the duration of the first and second periods for the input of the feeding solution and additional mixture flows to the reaction volume via the first and second porous barriers, the volume ratio of flows F31 and F32 is changed.

Example 6

Synthesis of chloramphenicol acetyl transferase (CAT) in the continuous exchange mode (CECF) in the translation system and in two variants of the combined transcription-translation systems.

It is known that transcription of a circular and linearized form of DNAs by phage polymerases proceeds in different conditions, in particular, at different $Mg^{2+}$ concentrations. Linear DNA templates can include plasmids linearized by restriction enzymes and PCR products. The use of PCR products excludes involvement of living cells for preparing genetic constructs (e.g., upon expression of genes coding for unstable or stable toxic products (Martemyanov et al., 1997)). Moreover, the use of PCR for preparing templates provides for an easier and more convenient modification of their constructs at the genetic level, including (a) introduction of elements stabilizing the RNA structure (e.g., highly structured regions, RQ elements of RNA, terminators of transcription etc.), (b) introduction of elements enhancing gene expression (e.g., enhancers, non-translatable leaders etc.), (c) introduction of coding marker sequences (e.g., epitopes, TAG for affinity isolation etc.).

The method provides for alterations in the intensity of transcription both from the circular plasmids that can be, for some reasons, in a supercoiled form and from plasmids having the form of a relaxed ring. For different polymerases, such forms are inherent to templates whose efficiency depends on $Mg^{2+}$.

Below is given an example of application of this method when circular plasmids are used upon CAT synthesis in the transcription-translation system.

To compare the productivity of synthesis in different modes, several reaction mixtures were used. The first reaction mixture was used to prepare the translation mixture, and CAT was synthesized using the earlier prepared mRNA. In the second mode, components for mRNA transcription were added to the reaction mixture and conditions were created for the combined transcription-translation. In the third variant, an additional mixture consisting of selected components, such as $Mg^{2+}$ and NTP, was added to the reaction mixture prepared for synthesis in the combined transcription-translation system. Additional components were introduced to the reaction mixture before the synthesis.

a) Synthesis of CAT in a Cell-free Translation System

The reaction mixture for mRNA translation was prepared taking into account the data given in Table 1. The mixture included a wheat germ extract.

TABLE 1

Composition of the reaction mixture for translation

| Components | Final concentration in the reaction mixture |
|---|---|
| Wheat germ extract | 30% v/v |
| CAT enhancer mRNA | 100 μg/ml |
| Yeast tRNA | 0.005 mg/ml |
| RNAse inhibitor | 133 U/ml |
| Protease inhibitor cocktail[1] 25-fold dilution | 1 X |
| 19 amino acids (each) | 0.1 mM |
| [$^{14}$C] Leucine, 38 mCi/mmol | 0.1 mM |
| ATP | 1 mM |
| GTP | 0.8 mM |
| Creatine-phosphate | 10 mM |
| HEPES-KOH pH 8.0[2] | 53 mM |
| KOAc[2] | 100 mM |
| $Mg(OAc)_2$[2] | 4.2 mM |
| DTT[2] | 1.3 mM |
| Spermidine | 0.1 mM |
| β-mercaptoethanol | 2 mM |
| Glycerol | 4% |
| $H_2O$ | to the final volume |

TABLE 1-continued

Composition of the reaction mixture for translation

| Components | Final concentration in the reaction mixture |
|---|---|

[1]Protease inhibitor cocktail "Complete", Boehringer Mannheim GmbH.
[2]Final concentrations take into account the contribution of concentrations of $Mg(OAc)_2$, KOAc, DTT, HEPES introduced by the wheat germ extract (Boehringer Mannheim GmbH).

The feeding solution was prepared according to the data given in Table 2.

TABLE 2

Composition of the feeding solution for translation

| Components | Final concentration in the feeding solution |
|---|---|
| HEPES-KOH pH 8.0 | 53 mM |
| KOAc | 100 mM |
| $Mg(OAc)_2$ | 4.2 mM |
| DTT | 1.3 mM |
| β-mercaptoethanol | 2.0 mM |
| Spermidine | 0.1 mM |
| ATP | 1.0 mM |
| GTP | 0.8 mM |
| Creatine-phosphate | 10 mM |
| Glycerol | 4% |
| [$^{14}$C]Leucine, 38 mCi/mmol | 0.1 mM |
| 19 amino acids (each) | 0.1 mM |
| $H_2O$ | to the final volume |

A dialyser prepared from a dialysis container of 8 mm in diameter (Union Carbide Corp.) and with the operation volume of 100 μl was used in this example. The volume of the feeding solution was 1 ml. To compare the productivity of the synthesis, the total reaction mixture was divided into two volumes. 30 μl of the reaction mixture were placed in a microcentrifuge tube, and 100 μl of the mixture were placed in the dialyser. The dialyser and the microtube were placed in a thermostated volume and synthesis was performed at 25° C. During the synthesis, 5 μl aliquots were taken from the microtube and the dialysis container to determine the kinetics of synthesis in the batch static mode and in the continuous exchange (CECF) mode. The amount of the synthesized polypeptide was determined by precipitation of the synthesized polypeptide on the glass fiber filter with trichloroacetic acid followed by radioactive counting in a liquid scintillation counter. FIG. 10 shows the kinetics of the synthesis. Diagram P refers to the synthesis in a batch mode. Diagram R demonstrates the kinetics of CAT synthesis upon translation in the CECF mode.

b) CAT Synthesis in the Combined Transcription-translation System

The reaction mixture was prepared in accordance with the data given in Table 3. The combined transcription-translation system contains the plasmid of pCAT enhancer with the gene of chloramphenicol acetyl transferase (CAT) under the SP6 polymerase promoter.

TABLE 3

Composition of the reaction mixture for the combined transcription-translation

| Components | Final concentration in the reaction mixture |
| --- | --- |
| Wheat germ extract | 30% v/v |
| pCAT-enhancer plasmid | 50 µg/ml |
| SP6 RNA polymerase | 15000 U/ml |
| Yeast tRNA | 0.005 mg/ml |
| RNAse inhibitor | 133 U/ml |
| Protease inhibitor cocktail[(1)] 25-fold dilution | 1 X |
| 19 amino acids (each) | 0.1 mM |
| [$^{14}$C] Leucine, 38 mCi/mmol | 0.1 mM |
| CTP | 0.4 mM |
| UTP | 0.4 mM |
| ATP | 1 mM |
| GTP | 0.8 mM |
| Creatine-phosphate | 10 mM |
| HEPES-KOH pH 8.0[(2)] | 53 mM |
| KOAc[(2)] | 100 mM |
| Mg(OAc)$_2$[(2)] | 5.0 mM |
| DTT[(2)] | 1.3 mM |
| Spermidine | 0.1 mM |
| β-mercaptoethanol | 2 mM |
| Glycerol | 4% |
| H$_2$O | to the final volume |

[(1)] and [(2)] are the same as in Table 1.

The feeding solution was prepared taking into account the data given in Table 4. To maintain the transcription process, CTP and UTP were added to the feeding solution.

TABLE 4

Composition of the feeding solution for transcription-translation

| Content | Final concentration in the feeding solution |
| --- | --- |
| HEPES-KOH pH 8.0[(2)] | 53 mM |
| KOAc | 100 mM |
| Mg(OAc)$_2$ | 5.0 mM |
| DTT | 1.3 mM |
| β-mercaptoethanol | 2.0 mM |
| Spermidine | 0.1 mM |
| ATP | 1.0 mM |
| GTP | 0.8 mM |
| CTP | 0.4 mM |
| UTP | 0.4 mM |
| Creatine-phosphate | 10 mM |
| Glycerol | 4% |
| [$^{14}$C] Leucine, 38 mCi/mmol | 0.1 mM |
| 19 amino acids (each) | 0.1 mM |
| H$_2$O | to the final concentration |

Conditions of the synthesis (temperature, reaction mixture volume, feeding solution volume, type of dialyser) were the same as those in Example 6a (CAT synthesis in the translation system). The results of the synthesis were analyzed as in Example 6a.

FIG. 11 shows the kinetics of CAT synthesis in the combined transcription-translation system. Diagram S represents synthesis in the batch mode. Diagram T represents the kinetics of CAT synthesis upon transcription-translation in the CECF mode.

c) CAT Synthesis in the Combined Transcription-translation System at a Continuous Change of Mg$^{2+}$ and NTP Concentrations in the Reaction Mixture During Synthesis The reaction mixture was prepared taking into account the data given in Table 5.

TABLE 5

Composition of the reaction mixture for the combined transcription-translation at a continuous change of Mg$^{2+}$ and NTP concentrations during synthesis

| Components | Final concentration in the reaction mixture |
| --- | --- |
| Wheat germ extract | 30% v/v |
| pCAT-enhancer plasmid | 50 µg/ml |
| SP6 RNA polymerase | 15000 U/ml |
| Yeast tRNA | 0.005 mg/ml |
| RNAse inhibitor | 133 U/ml |
| Protease inhibitor cocktail[(1)] 25-fold dilution | 1 X |
| 19 amino acids (each) | 0.1 mM |
| [$^{14}$C] Leucine, 38 mCi/mmol | 0.1 mM |
| CTP | 0.8 mM |
| UTP | 0.8 mM |
| ATP | 2.0 mM |
| GTP | 1.6 mM |
| Creatine-phosphate | 10 mM |
| HEPES-KOH pH 8.0[(2)] | 53 mM |
| KOAc[(2)] | 100 mM |
| Mg(OAc)$_2$[(2)] | 11.2 mM |
| DTT[(2)] | 1.3 mM |
| Spermidine | 0.1 mM |
| β-mercaptoethanol | 2 mM |
| Glycerol | 4% |
| H$_2$O | to the final volume |

[(1)], [(2)] are the same as in Table 1.

The feeding solution is prepared with account for the data given in Table 6.

TABLE 6

Composition of the feeding solution for the combined transcription-translation at a continuous charge of Mg$^{2+}$ and NTP concentrations during synthesis

| Components | Final concentration in the feeding solution |
| --- | --- |
| HEPES-KOH pH 8.0 | 53 mM |
| KOAc | 100 mM |
| Mg(OAc)$_2$[(1)] | 3.8 mM |
| DTT | 1.3 mM |
| β-mercaptoethanol | 2.0 mM |
| Spermidine | 0.1 mM |
| ATP | 1.0 mM |
| GTP | 0.8 mM |
| CTP | 0.4 mM |
| UTP | 0.4 mM |
| Creatine-phosphate | 10 mM |
| Glycerol | 4% |
| [$^{14}$C] Leucine, 38 mCi/mmol | 0.1 mM |
| 19 amino acids (each) | 0.1 mM |
| H$_2$O | to the final volume |

The concentration of Mg(OAc)$_2$ in the feeding solution was reduced to 3.8 mM, since during the synthesis when the concentrations of the reaction mixture and the feeding solution become the same, the concentration of Mg(OAc)$_2$ raises to 5.1 mM which is appropriate to transcription-translation.

Conditions of the synthesis (temperature, volume of the reaction mixture and that of the feeding solution, type of dialyser) were selected analogous to those given in Example 6a (CAT synthesis upon translation). The results of the synthesis were analyzed as described in Example 6a.

FIG. 12 shows the kinetics of CAT synthesis in the combined transcription-translation system. Diagram U represents synthesis in the batch mode. Diagram V represents the kinetics of CAT synthesis upon transcription-translation in the CECF mode with changing concentrations of the $Mg^{2+}$ and NTP in the reaction mixture during the synthesis.

FIG. 13 shows a diagram which compares the results of experiments on the synthesis of the target CAT polypeptide. The data are taken from examples 6a–c and demonstrate the yield of CAT (µg/ml) in different modes: (a) static (batch) mode of combined transcription-translation (example 6b, bar W); (b) translation (example 6a, bar X); (c) combined transcription-translation (example 6b, bar Y); (d) combined transcription-translation with changing concentrations of $Mg^{2+}$ and NTP in the reaction mixture (example 6c, bar Z). A comparison of the results shows that the highest yield of CAT polypeptide (32 µg/ml) is obtained in the combined transcription-translation mode when concentrations of $Mg^{2+}$ and NTP are changed from their maximal to minimal values.

INDUSTRIAL APPLICABILITY

The invention can be used to synthesize polypeptides in cell-free systems using eukaryotic and prokaryotic cells. The method described herein allows the user to optimize the entire synthesis and to study the contribution of individual components to the synthesis at separate modes of transcription, transcription-translation and translation.

REFERENCES

Alakhov J. B. et al. Method of preparing polypeptides in a cell-free translation system. U.S. Pat. No. 5,478,730, U.S. CI. 435/68.1 (Dec. 26, 1995)

Alakhov J. B. et al. Method of obtaining polypeptides in cell-free translation system. EP Patent 0312617, Int. CI. C12P 21/00 (Mar. 3, 1993)

Alberts B. et al. Molecular biology of the cell. New York, London. p. 133 (1983)

Baranov V. I. et al. Gene expression in a cell-free system on the preparative scale. Gene 84: 463–466 (1989)

Baranov V. I. et al. Method for obtaining polypeptides in a cell-free system. EP Patent 0593757, Int. CI. C12P 21/00 (Jan. 15, 1997)

Baranov V. I. et al. Method for preparative expression of genes in a cell-free system of conjugated transcription/translation. EP Patent 0401369, Int. CI. C12P 21/00 (31.05.1995)

Baranov V. I., Spirin A. S. Gene expression in cell-free system on preparative scale. From: "Methods in Enzym." Vol. 217 "Recombinant DNA", Part H, Edit. R. Wu, Academic Press p.p. 123–142 (1993)

Bauer H. et al. Verfaren und forrichtung zur Durchführung biochemicher Reaktionen. DE Patent Appl. 19832160.0 A1, Int. CI. C12M 1/12 (Feb. 4, 1999)

Beckler G. S. Coupled transcription and translation in eukaryotic cell-free extract. U.S. Pat. No. 5,324,637, U.S. CI. 435/68.1 (Sep. 9, 1999)

Choi C. et al. Method producing protein in a cell-free system. U.S. Pat. No. 5,593,856. U.S. CI. 435/68.1 (Jan. 14, 1997)

Clark C. Dialysis device with hermetically sealed vacant chamber. U.S. Pat. No. 5,503,741, U.S. CI. 210/232 (Apr. 2, 1996)

Craig D. et al. Plasmid cDNA-directed protein synthesis in a coupled eukaryotic in vitro transcription-translation system, Nucl. Acids Res. V. 20, No. 19: 4987–4995 (1993)

Davis J. et al. Large scale dialysis reactions using E. coli S30 extract systems Promega Notes N 56: 14–20 (1996)

Dziewulski D. et al. Three compartment bioreactor and method of use. U.S. Pat. No. 5,135,853, U.S. CI. 435/04 (Apr. 4, 1992)

Erdmann V. A. et al., The Protein—Bioreactor: Its Potentials for the Synthesis of Proteins in Biotechnology, Medicine and Molecular Biology. First German-Russian Summer school on In vitro Systems, 64–70, Berlin (1994)

Fischer K., Bauer H. Verfahren zur Beschieunigung des Stoffaustauschs eines kontinuierlichen Bioreaktors und Vorrichtung zur Durchführung dieses Verfahrens, DE Patent Appl. 3914956 A1, IPC CI. C12M 1/12 (Nov. 22, 1990)

Flaherty J. E. Disposable dialysis apparatus. U.S. Pat. No. 5,324,428, U.S. CI. 210/232 (Jun. 28, 1994)

Guajardo R. et al. NTP Concentration Effects on Initial Transcription by T7 RNAP Indicate that Translocation Occurs through Passive Sliding and Reveal that Divergent Promoters have Distinct NTP Concentration Requirements for Productive Initiation. J. Mol. Biol. 281, 777–792 (1998)

Gurevich V. et al. Preparative in-Vitro mRNA Synthesis Using SP6 and T7 RNA Polymerases. Analyt. Biochem. 195: 207–213 (1991)

Joice G. F. Coupled isothermal polynucleotide amplification and translation system. U.S. Pat. No. 5,807,717, U.S. CI. 435/091.1 (Sep. 15, 1998)

Kern J. A., Davis R. H. Application of solution equilibrium analysis to in-vitro RNA transcription. Biotechnol. Prog., 13: 747–756 (1997)

Kim D. M., Choi C. Y. A semicontinuous prokaryotic coupled transcription/translation system using a dialysis membrane. Biotechnol. Prog., September, 12: 645–649 (1996)

Laios E. et al. Novel hybridization assay configurations based on in vitro expression of DNA reporter molecules. Clin. Biochem, April, 31: 3, 151–158 (1998)

Maier T. et al. Streptag II affinity purification: an approach to study intermediates of metalloenzyme biosynthesis. Anal. Biochem. 259:1, 68–73 (1998)

Martemyanov K. A. et al. Direct expression of PCR products in a cell-free transcription/translation system: synthesis of antibacterial peptide cecropin. FEBS Letters 414: 268–270 (1997)

Merrick W. C. Translation of Exogenous mRNAs in Reticulocyte Lysates. From: "Methods in Enzymology" Vol. 101: "Monitoring cloned gene expression" Academic Press, Inc. p.p.606–615 (1983)

Mozayeni B. R. Apparatus and process for continuous in vitro synthesis of proteins. U.S. Pat. No. 5,434,079, U.S. CI. 435/311 (Jul. 18, 1995)

Operating Guide, Linked in vitro SP6/T7 Transcription/Translation Kit. Roche Diagnostics GmbH (1998)

Operating Guide, Single Tube Protein™ System 3. Novagen Inc. (1998)

Ovodov S. J. et al. Method for obtaining polypeptides in a cell-free translation system. EP Patent 0485608, Int. CI. C12P 21/00 (Nov. 22, 1995)

Palmenberg A. C. et al. Translation enhancer. U.S. Pat. No. 4,937,190, U.S. CI. 435/69.1 (Jun. 26, 1990)

Pelham H. R. B., Jackson R. J. An efficient mRNA-dependent translation system from reticulocyte lysates. Eur. J. Biochem. V. 67: 247–256 (1976)

Pokrovskaya I., Gurevich V. In-vitro Transcription: Preparative RNA Yields in Analytical Scale Reactions. Analyt. Biochem. 220: 420–423 (1994)

Roberts B. E. Protein translation method. U.S. Pat. No. 4,668,624, U.S. CI. 435/68 (Mar. 28, 1979)

Roberts B. E., Paterson B. M. Efficient translation of tobacco mosaic virus RNA and rabbit globin 8S RNA in a cell-free system from commercial wheat germ. Proc. Natl. Acan. Sci. U.S.A. 70: 2330–2334 (1973)

Ryabova L. A. et al. Continuous-flow cell-free translation, transcription-translation, and replication-translation systems. From: "Methods in Molecular Biology" Vol.77 "Protein Synthesis: Methods and Protocols". Edit. R. Martin, Humana Press Inc. Totowa, N.J. p.p. 179–193 (1998)

Ryabova L. A. et al. Preparative synthesis of globin in a continuous cell-free translation system from rabbit reticulocytes. Nucleic Acids Res. 17, 11: 4412 (1989)

Sakurai T. Method for production protein in cell-free system and device therefore. JP Patent 7031494, IPC CI. C12P 21/00 (Feb. 3, 1995)

Sato T. Method for synthesizing polypeptide. JP Patent 5076381, IPC CI. C12P 21/00 (Mar. 30, 1995)

Shimizu N. Method for synthesizing protein by extracted solution of cell and device therefore. JP Patent 7075592, IPC CI. C12P 21/00 (Mar. 20, 1995)

Spirin A. S. Cell-Free Protein Synthesis Bioreactor. From: "Frontiers in Bioprocessing II", Edit. Todd P. et al , Amer. Chemic. Soc. p.p. 31–43 (1992)

Spirin A. S. et al. A Continuous Cell-Free Translation System Capable of Producing Polypeptides in High Yield. Science, 242: 1162–1164 (1988)

Suzuki H. Effect of Concentration of KCL, Magnesium Acetate and Spermine on the Ratio of α to β Globin Chains Synthesized. J. Biochem, 82:1, 251–260 (1977)

Takanori K. et al. A Continuous Cell-Free Protein Synthesis System for Coupled Transcription-Translation. J. Biochem. 110; 166–168 (1991)

Thompson D. V. et al. Coupled transcription and translation in eukaryotic cell-free extract. U.S. Pat. No. 5,324,637, U.S. CI. 435/68.1 (Jun. 28, 1994)

Volyanik E. V. et al. Synthesis of Preparative Amounts of Biologically Active interleukin 6 Using a Continuous-Flow Cell-Free Translation System. Analyt. Biochem. 214; 289–294 (1993)

Wimmer E. et al. De novo cell-free synthesis of picomavirus. U.S. Pat. No. 5,6747,29, U.S. CI. 435/235.1 (Oct. 7, 1997)

Yamamoto Y., et al. Hollow fiber reactor for continuous flow cell-free protein production. J. Chem. Eng. Japan, 6:1047–1050 (1996)

Yamane T. et al. Synthesis of protein by cell-free protein synthetic system and apparatus therefore. JP Patent 10080295, IPC CI. C12P 21/00 (Mar. 31, 1998)

Zubay G. In vitro synthesis of protein in microbial systems. Annu. Rev. Genet. 7: 267–287 (1973)

What is claimed is:

1. A method for obtaining polypepoides in a cell-free system by which the reaction mixture is prepared with the use of a cell lysate or cell extract, the parameters of the cell-free system and the mode of synthesis are chosen, the type and parameters of at least one porous barrier are determined, the reaction mixture and the feeding solution are placed in the reaction module, and the synthesis is performed, wherein upon the parameters of the process are chosen, the types of the selected components determining the productivity of the synthesis are selected, the upper and lower limits of the range within which the concentrations of the selected components are changed during the synthesis are defined, the additional mixture containing the selected components is formed, the additional mixture is supplied to the reaction mixture or to the feeding solution, the synthesis is performed with changing concentrations of the selected components within the defined ranges while the concentrations of the other components are maintained constant.

2. The method according to claim 1 wherein at least one of the selected components is chosen from the group consisting of $Mg^{2+}$, $K^+$, NTP, polyamine or their combination.

3. The method according to claim 2 wherein one combination of the selected components includes $Mg^{2+}$ and NTP.

4. The method according to claim 1 wherein the mode of synthesis is chosen at least from one mode selected from a group consisting of translation, transcription-translation, transcription or combinations of these modes.

5. The method according to claim 4 wherein depending on the mode of synthesis, NTPs contained in the additional mixture consist of a group of ATP, GTP, UTP and CTP or a group of ATP and GTP.

6. The method according to claim 1 wherein the additional mixture is supplied to the reaction mixture before the synthesis or during the synthesis, or the additional mixture is supplied to a part of the feeding solution before the synthesis or during the synthesis.

7. The method according to claim 6 wherein the additional mixture is supplied once, recurrently or continuously during the synthesis.

8. The method according to claim 1 wherein the mode of input of low molecular weight components of the feeding solution to the reaction mixture is selected from a group of continuous exchange modes, a group of continuous flow modes, or a combination of these modes.

9. The method according to claim 1 wherein the reaction mixture is prepared using a cell lysate or cell extract obtained from prokaryotic or eukaryotic cells.

* * * * *